(12) United States Patent
Agee et al.

(10) Patent No.: US 7,718,058 B2
(45) Date of Patent: May 18, 2010

(54) CHROMATOGRAPHY COLUMN WITH PACK, UNPACK, AND CLEAN-IN-PLACE FEATURES

(75) Inventors: Maurice Agee, Yssac-la-Tourette (FR); Sebastien Lefebvre, Saint Saturnin (FR); Sebastien Magnaud, Lezoux (FR); Philippe Vernot, Aulhat Saint Privat (FR)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 12/107,916

(22) Filed: Apr. 23, 2008

(65) Prior Publication Data
US 2008/0264837 A1 Oct. 30, 2008

Related U.S. Application Data

(60) Provisional application No. 60/913,919, filed on Apr. 25, 2007.

(51) Int. Cl.
*B01D 15/08* (2006.01)
(52) U.S. Cl. ............ 210/198.2; 210/281; 210/656
(58) Field of Classification Search ........... 210/198.2, 210/656, 659, 281; 95/82; 96/101
See application file for complete search history.

(56) References Cited

U.S. PATENT DOCUMENTS

| | | | |
|---|---|---|---|
| 4,168,235 A * | 9/1979 | Guillemin et al. ......... | 210/198.2 |
| 4,263,144 A * | 4/1981 | Platt ......................... | 210/658 |
| 4,288,322 A * | 9/1981 | Guillemin et al. ......... | 210/198.2 |
| 4,379,751 A | 4/1983 | Yoritomi et al. | |
| 4,437,487 A * | 3/1984 | Marmon ..................... | 137/322 |
| 4,836,236 A | 6/1989 | Ladisch | |
| 4,994,180 A * | 2/1991 | Sims et al. ................. | 210/198.2 |
| 5,441,079 A | 8/1995 | Zimmerly | |
| 5,479,955 A | 1/1996 | Roodvoets et al. | |
| 5,904,173 A | 5/1999 | Ozawa | |
| 6,117,317 A * | 9/2000 | Dickson et al. ........... | 210/198.2 |
| 6,123,849 A * | 9/2000 | Purdom ..................... | 210/656 |
| 6,558,539 B1 * | 5/2003 | Mann ......................... | 210/198.2 |

(Continued)

FOREIGN PATENT DOCUMENTS

WO WO 2005/080962 * 9/2005

*Primary Examiner*—Ernest G Therkorn
(74) *Attorney, Agent, or Firm*—Townsend and Townsend and Crew LLP.; M. Henry Heines

(57) ABSTRACT

A preparative chromatography column is equipped with one or more valves that can each be used to both inject a column packing into the column or withdraw used packing from the column, in addition to cleaning the supply and discharge lines associated with the valve itself, all by moving a movable plug within the valve body and all without protruding into the column interior. Each valve is mounted on the lateral wall of the column just above the filter plate at the column floor, and the plug is movable between a closed position in which the end surface of the plug is flush with the inner wall of the column and an open position in which the plug is recessed within the bore. Each valve has two additional ports in its valve body, positioned such that when the plug is closed, both ports are open to the valve bore, and when the plug is open, at least one of the ports is open to the bore. The position of the plug within the valve bore determines the valve function.

4 Claims, 4 Drawing Sheets

U.S. PATENT DOCUMENTS

| | | | |
|---|---|---|---|
| 6,645,377 B1 * | 11/2003 | Egorov et al. | 210/198.2 |
| 6,740,241 B1 * | 5/2004 | Dickson | 210/656 |
| 7,001,522 B2 * | 2/2006 | Egorov et al. | 210/656 |
| 2003/0098280 A1 * | 5/2003 | Davis et al. | 210/656 |
| 2004/0251206 A1 * | 12/2004 | Egorov et al. | 210/656 |
| 2007/0193933 A1 * | 8/2007 | Vidalinc | 210/198.2 |

* cited by examiner

CHROMATOGRAPHY COLUMN WITH PACK, UNPACK, AND CLEAN-IN-PLACE FEATURES

CROSS-REFERENCE TO RELATED APPLICATION

This application claims the benefit of U.S. Provisional Patent Application No. 60/913,919, filed Apr. 25, 2007, the contents of which are incorporated herein by reference in their entirety.

BACKGROUND OF THE INVENTION

1. Field of the Invention

This invention resides in the field of preparative chromatograph columns, and in particular, the components associated with such columns for filling the columns with packed beds of separation media, removing such media from the columns, and cleaning the columns between uses.

2. Description of the Prior Art

Preparative chromatography is the use of chromatographic separation principles to isolate individual chemical species from mixtures at quantities sufficient for use of the isolated species on a commercial scale, rather than for analytical purposes. One of the various types of equipment in which preparative chromatography is performed is a large-diameter vertical column containing a packed bed of solid or semi-solid separation medium serving as a stationary phase. The mixture from which the species of interest is to be isolated is passed through the column by way of a mobile phase that flows through the packed bed in a generally plug-flow regime. The width of the column is sufficient, exceeding 1 meter in some cases, to accommodate a commercially useful throughput rate, while the depth of the column is limited to maintain a pressure drop that is low enough to avoid the need for a high pump pressure or high pumping power. Columns of this type contain a plunger or piston head that is lowered to contact and compress the solid phase to the desired height. The mobile phase enters the column through the plunger which includes a distributor plate to spread the mobile phase across the full width of the bed. At the floor of the column is a plate that includes a filter, a distribution system, and a fluid port. The pore size of the filter is smaller than the particle size of the packed bed, thus retaining the packed bed in the column, yet large enough to allow the mobile phase to pass. The distribution system at the column floor ensures that the mobile phase leaving the column is drawn from the full width of the column, the top and bottom distribution systems together ensuring that maximal use is made of the bed.

The use of a preparative chromatography column of this type requires that the packed bed be periodically removed and replaced and that the column itself and its various supply and discharge lines be cleaned. With large diameter columns, these operations typically require opening of the column and other operations that are costly both in labor and capital. These concerns are particularly acute when operation of the column requires a clean room or a high clearance above the column, or both.

SUMMARY OF THE INVENTION

The present invention resides in a preparative chromatography column that can be filled with a slurry of the stationary phase and then emptied of the stationary phase, and whose supply and discharge lines can be flushed and cleaned, all though a common valve, or preferably a series of such valves distributed around the column each of which is capable of performing each of these functions. Each valve is mounted at an aperture in the lateral wall of the column that is substantially level with the upper surface of the filter plate at the column floor, and each valve has an internal bore and a movable plug slidably retained within the bore. The plug is movable between a closed position in which the end surface of the plug obstructs the aperture in the column wall and is substantially flush with the inner surface of the column and an open position in which the end surface of the plug is recessed within the bore, allowing flow communication between the bore and the aperture. In neither position does the plug protrude into the column interior, obstruct the flow of mobile phase within the column, or compress the stationary phase in the column interior. Each valve, in addition to its opening directly into the column, has two ports in its valve body. The ports are positioned in the valve body such that when the plug is in its closed position, both ports are open, thereby allowing flow communication between the two ports and through the bore. The ports and the bore can thus be flushed and cleaned without disturbing the column contents or the column operation. When the plug is in its open position, at least one of the ports is open to the bore, thereby allowing media to enter the column through that port, then through the valve bore, and through the column wall aperture. In certain embodiments, the plug, when in its open position, closes off the second port, leaving only the first port for supply to or discharge from the column. In other embodiments, both ports remain open regardless of the position of the plug, so that supply, discharge and cleaning can be accomplished through both ports and the aperture simultaneously, or so that each port can be used individually for these purposes by closing off the other port by a closure that is external to the valve. As will be seen from the discussion that follows, the ports, the plug, and the valve body can assume a variety of configurations, all embodying the central concept of a single valve serving multiple functions and allowing the column to be filled and emptied, and the supply and discharge lines cleaned, by simply moving a plug that is internal to the valve body.

DETAILED DESCRIPTION OF THE INVENTION AND PREFERRED EMBODIMENTS

Figure 1:
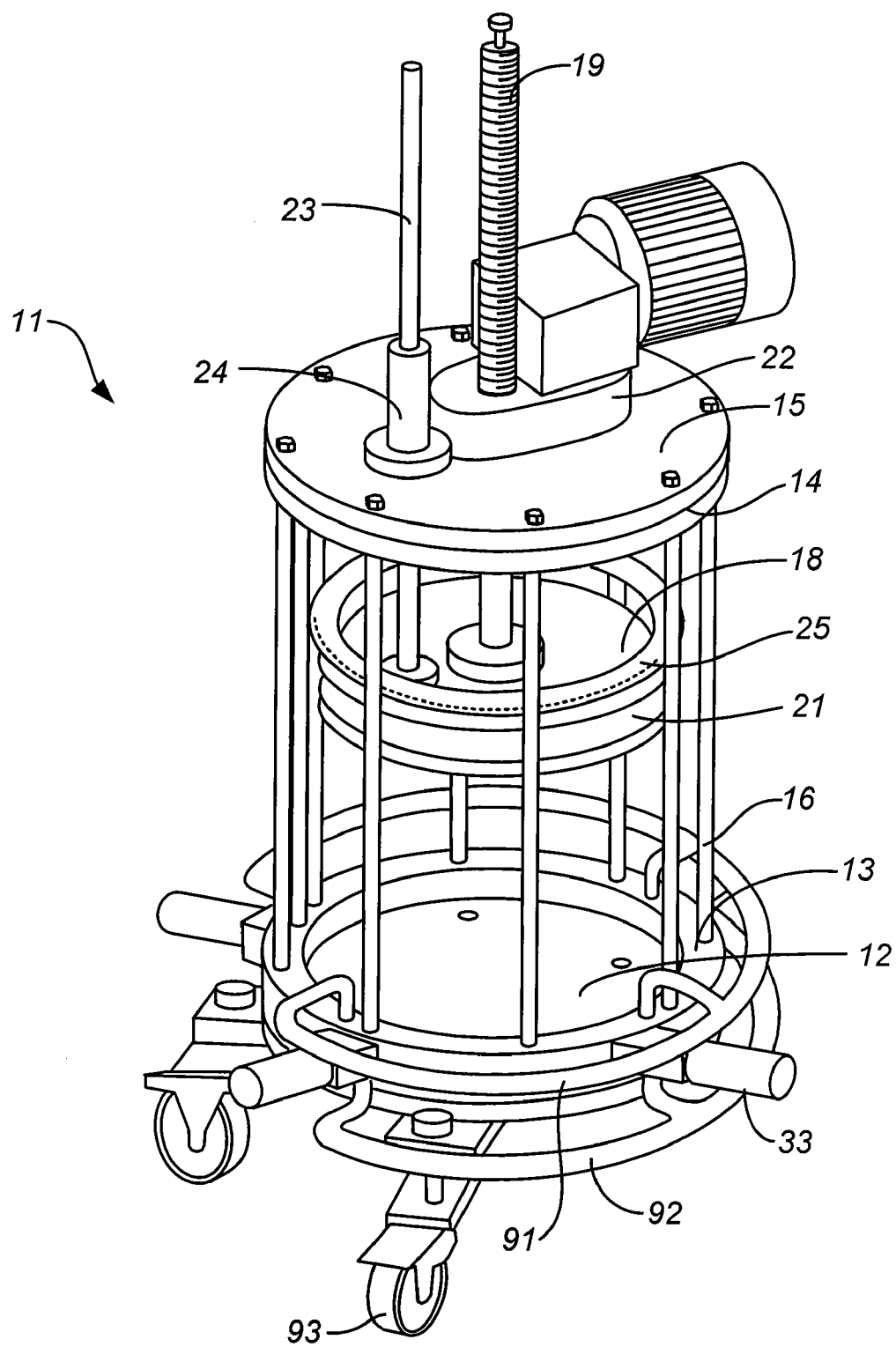
FIG. 1 is a perspective view of a column support for a preparative chromatography column incorporating features of the present invention.

While the features defining this invention are capable of implementation in a variety of constructions, the invention as a whole will be best understood by a detailed examination of specific embodiments. Three such embodiments are shown in the drawings.

FIG. 1 depicts a column support or skid 11 incorporating features of the present invention. The base of the column support includes a base plate 12 with a lower ring 13 secured to the upper surface of the base plate, and the top of the support includes an upper ring 14 and top plate 15 secured to the upper surface of the upper ring. A series of supporting rods 16 (eight in this embodiment) support the upper ring 14 above the lower ring 13 and are equally spaced around the rings to form a circle. The column tube (not shown in this Figure) is a cylinder open at the top and bottom that is received within the circle of supporting rods 16, resting on the lower ring 13. A plunger 18 is mounted on the end of a shaft 19 that extends through the top plate 15 and upper ring 14, with the plunger itself inside the column tube to serve as the upper closure of the column. The plunger 18 is movable vertically and sets the height of the separation medium in the column, and is accordingly also referred to as an adaptor or a piston. In use, the plunger 18 is lowered to contact the separation medium and compress the medium to the desired height. The movement of the plunger and the force applied by the plunger are controlled by an electric, hydraulic, or pneumatic actuator. Secured to the plunger 18 is a circumferential gasket 21 that is inflatable and seals against the inner surface of the column tube.

In this embodiment, the shaft 19 that supports the plunger 18 is a hollow rod that is threaded on its outer surface. With its hollow center, the shaft 19 serves as a process line to supply the mobile phase to the column, and the external threads of the shaft, in conjunction with a gear box 22, form a worm gear for moving the plunger shaft 19 and hence the plunger 18 up and down. In other embodiments, the process line is mounted outside the shaft 19.

A further feature shown in FIG. 1 is a guide shaft 23 which extends upward from the plunger 18 and passes through an aperture in the top plate 15 surrounded by a sleeve 24. The guide shaft 23 prevents the plunger 18 from rotating and can be graduated to indicate the height of the plunger 18 inside the column tube and hence the height of the separation medium. A still further feature is a tube 25 positioned above the plunger 18, the tube containing spray nozzles directed downward toward the peripheral edge of the plunger 18. When the circumferential gasket 21 is deflated, the spray nozzles can be pressurized to rinse adhering media particles from the edge of the gasket.

Figure 2A:
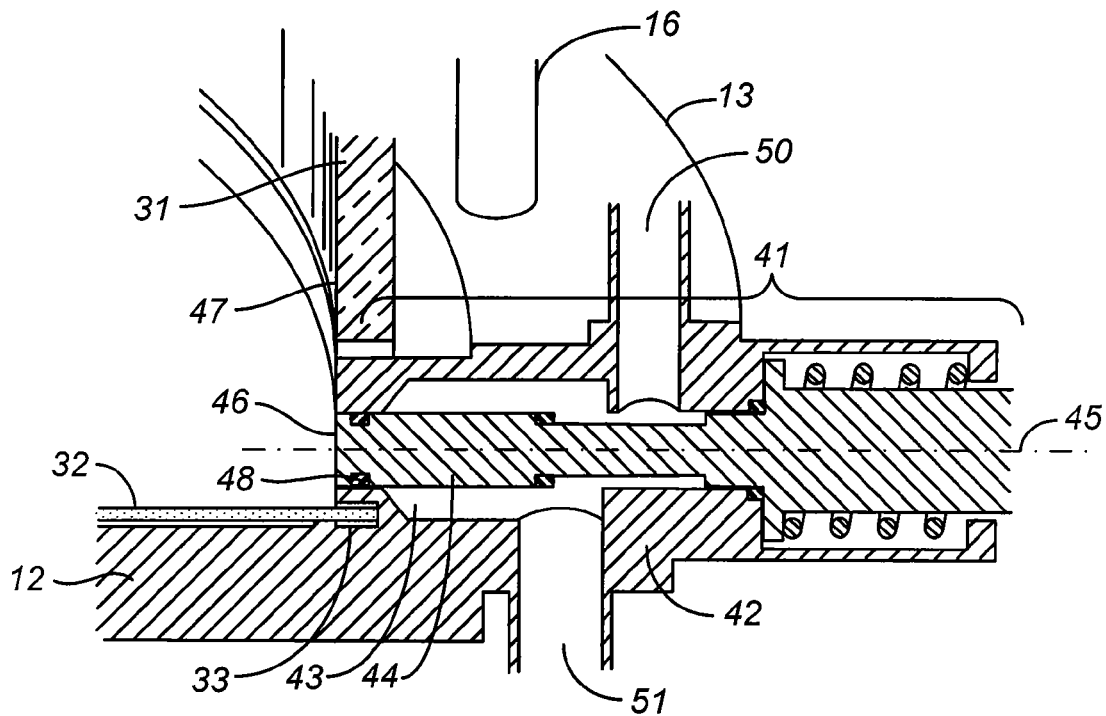
FIG. 2a is a cross section of one example of an injection-drainage valve in accordance with the present invention, with the valve plug in the closed position.
Figure 2B:
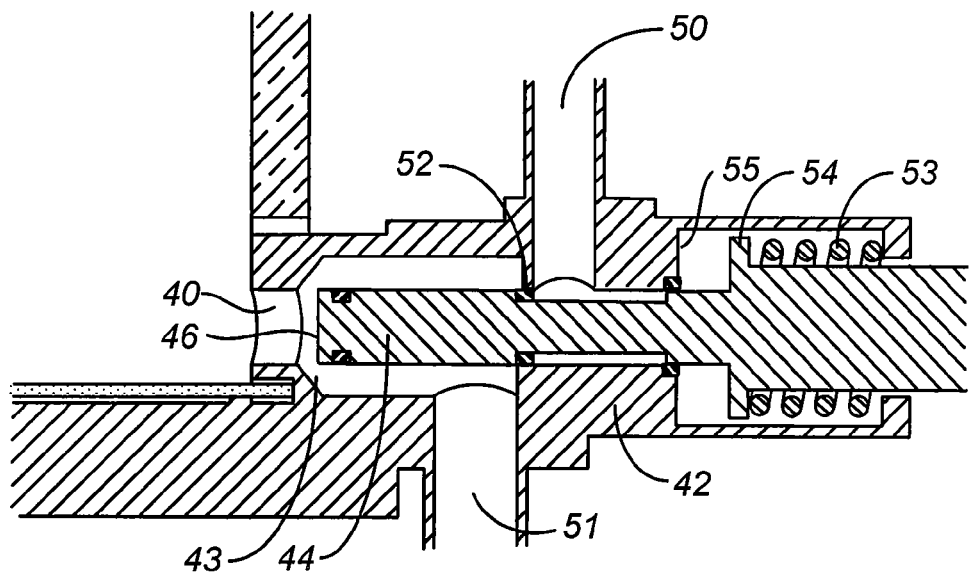
FIG. 2b is the same view of the same valve with the valve plug in the open position.

FIGS. 2a and 2b show the column cylinder 31 and structural features of the lower end of the column support. A filter 32 is positioned over the base plate 12 with the peripheral edge of the filter 32 held between the base plate 12 and the lower ring 13 where the peripheral edge of the filter 32 is sealed by a U-shaped gasket 33. FIGS. 2a and 2b also show one of the apertures 40 (FIG. 2b) in the column wall, positioned substantially at the level of, and just above, the filter 32, and a valve 41 that opens into the aperture and provides the multiple functions described above, i.e., supplying and removing the stationary phase from the column and flushing the column as well as the valve itself and the lines to and from the valve with wash solution. The number of valves is not critical and can vary, depending on the size of the column. The embodiment shown in FIG. 1 includes four such valves evenly spaced around the lower ring 13.

The valve 41 is constructed of a valve body 42 with a bore 43 and an elongated movable plug 44 within the bore. The geometry of the bore 43 defines a bore axis 45 and the range of motion of the plug 44 is along the bore axis 45. The plug is shown at the two extreme ends of its range of motion in the two Figures, respectively. In the closed position of the plug shown in FIG. 2a, the end surface 46 of the plug closes the aperture and is substantially flush with the interior surface 47 of the column wall, providing an essentially smooth contour with the surrounding surface of the wall. An o-ring gasket 48 encircles the plug near the end surface 45 to help seal the plug in the aperture. The two additional ports 50, 51 in the valve body are both lateral ports with axes transverse to the bore axis 45. These ports are arranged in the valve body such that when the valve is in the closed position shown in FIG. 2a, both ports 50, 51 are open to the bore 43, and wash fluid can be fed through one of the two ports to flush out both ports and the bore, without entering the column. In the open position of the plug 44 as shown in FIG. 2b, the end surface 46 of the plug is recessed inside the bore 43 and retracted from the aperture 40. This opens a passage from the column interior through the bore and out one of the two ports 51 for emptying and drainage of the column, or alternatively allows the column to be filled through the same port 51. In either case, the upper port 50 is closed from the aperture 40 and the lower port 51, and the seal is enhanced with a o-ring gasket 52. Even though the mouth of the upper port 50 in this embodiment is not itself closed by the plug 44, the port is effectively closed since the valve provides no outlet or communication between the port 50 and either the other port 51 or the aperture 40. The valve body 42 contains an internal coil spring 53 that biases the plug 44 toward its closed position (FIG. 2a), and a flange 54 extends radially from the plug 44 to engage the coil spring 53 and an internal shoulder 55 to contain the plug 44 and limit the range of motion. The plug 44 can be retracted against the spring 53 by conventional means such as a pneumatic valve, a solenoid valve, a mechanical, hand-operated lever, or any other mechanisms that will be readily apparent to those skilled in the art.

Figure 3A:
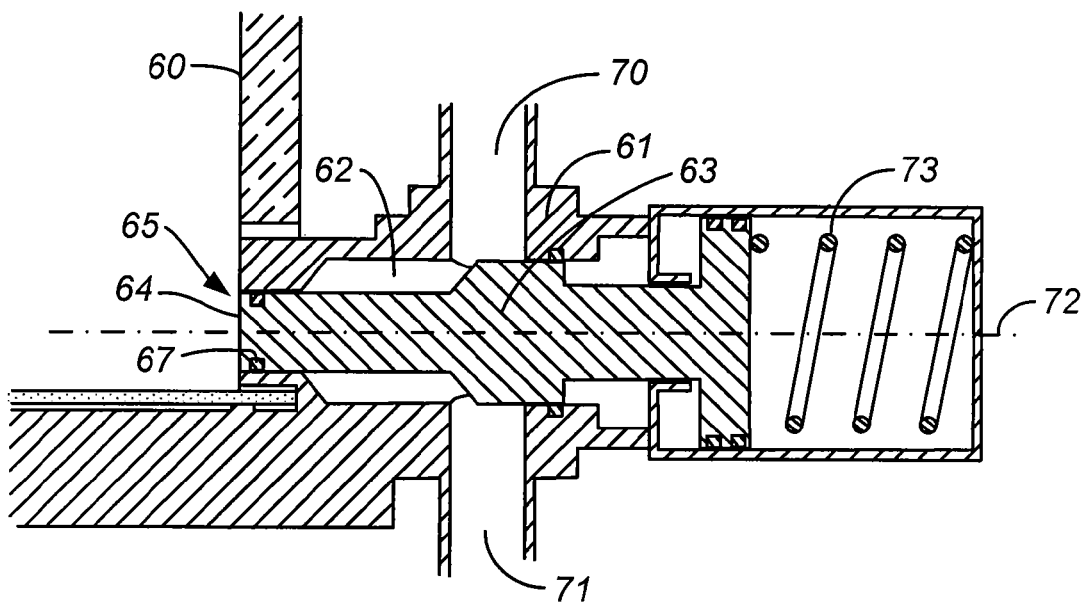
FIG. 3a is a cross section of a second example of an injection-drainage valve in accordance with the present invention, with the valve plug in the closed position.
Figure 3B:
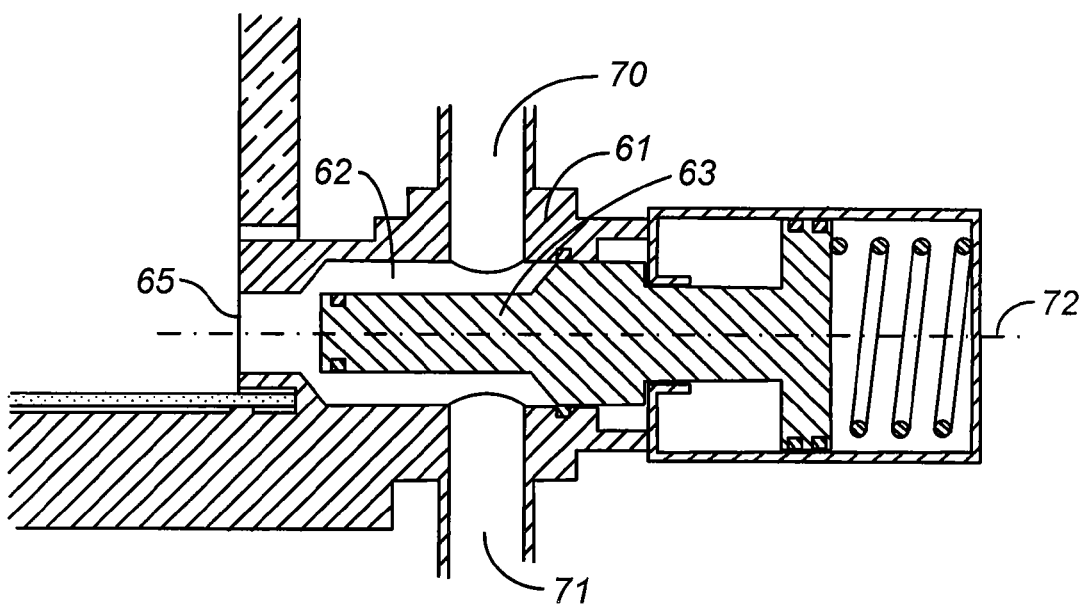
FIG. 3b is the same view of the same valve with the valve plug in the open position.

The valve of FIGS. 3a and 3b is a variation on the valve of FIGS. 2a and 2b. The valve of FIGS. 3a and 3b, likewise shown in the closed-plug position in FIG. 3a and in the open-plug position in FIG. 3b, similarly includes a valve body 61, a bore 62, and a movable plug 63. Similarly as well, when the plug is in the closed position of FIG. 3a, the end surface 64 of the plug closes the aperture 65 and is substantially flush with the interior surface 66 of the column wall. An o-ring gasket 67 encircles the plug near the end surface 64 to help seal the plug in the aperture. The two additional ports 70, 71 in the valve body are both lateral ports with axes transverse to the bore axis 72. In this embodiment, however, unlike that of FIGS. 2a and 2b in which the lateral ports 50, 51 are not aligned with each other, the lateral ports 70, 71 are indeed aligned with each other, and due to the symmetrical shape of the plug 63 around the bore axis 72, both lateral ports 70, 71 are at least partially open at all positions of the plug 63. Thus, when the plug 63 is in the open position of FIG. 3b, both lateral ports 70, 71 are in flow communication with the aperture 65, and filling and emptying of the column can both be performed through either of both of the lateral ports. Flow through either port can be prevented by operation of separate shut-off valves (not shown) on the lines that are external to the valve. A coil spring 73 housed inside the valve body 61 operates in a manner analogous to the coil spring 53 of the valve of FIGS. 2a and 2b.

Figure 4A:
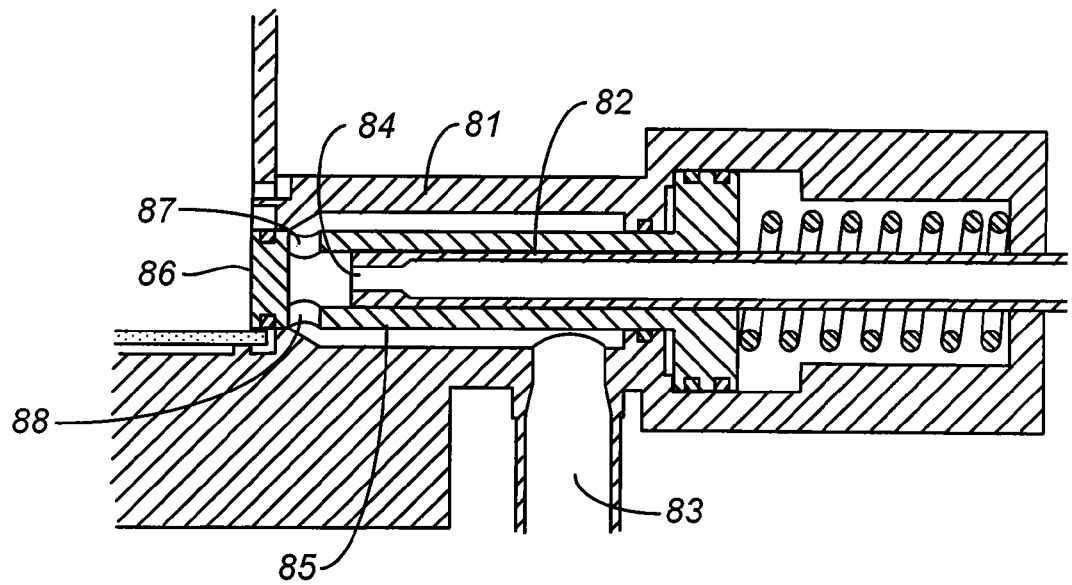
FIG. 4a is a cross section of a third example of an injection-drainage valve in accordance with the present invention, with the valve plug in the closed position.
Figure 4B:
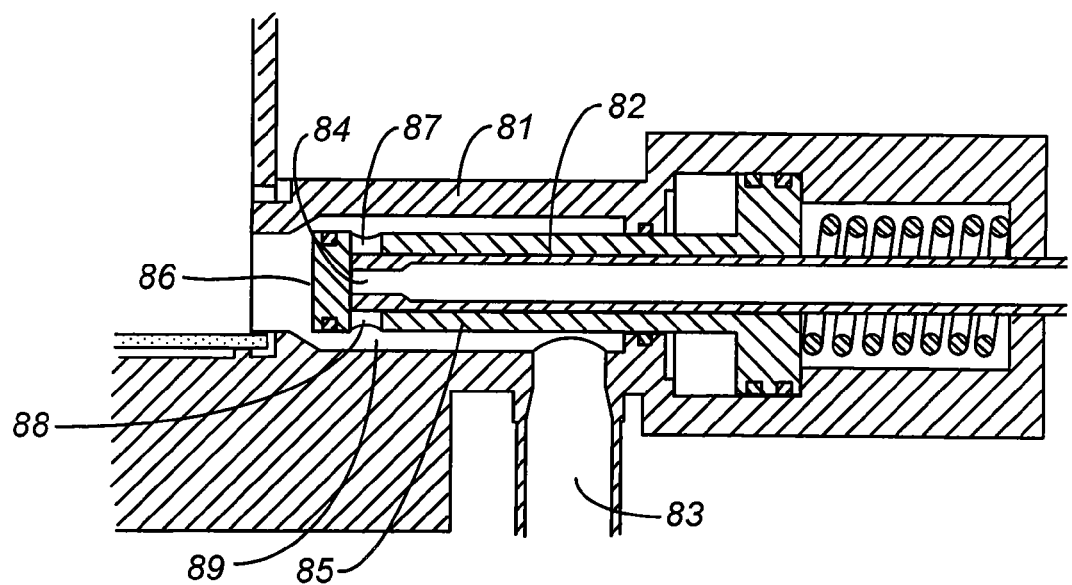
FIG. 4b is the same view of the same valve with the valve plug in the open position.

FIGS. 4a and 4b illustrate another variation. In this case, the valve body is constructed in two parts—a shell 81 and a hollow tube 82 within the shell and rigidly secured to the shell. Instead of two lateral ports as in the examples shown in FIGS. 2a, 2b, 3a, and 3b, the valve contains a single lateral port 83 and an internal axial port 84 at the terminus of the hollow tube 82. The movable plug in this embodiment is a sleeve 85 that encircles and slides over the hollow tube 82. The sleeve 85 is closed at the end to form an end surface 86 analogous to the end surfaces 46, 64 of the plugs of valves of FIGS. 2a, 2b, 3a, and 3b, respectively. Thus, with the sleeve 85 in the closed or extended position shown in FIG. 4a, the sleeve end closes the aperture and the end surface 86 is flush with the inner wall surface of the column. The sleeve 85 itself contains lateral apertures 87, 88 arranged such that when the sleeve is in its extended position as shown in FIG. 4a, a passage exists that extends from the interior of the hollow tube 82 through the internal port 84 at the end of the hollow tube, through the lateral apertures 87, 88 in the sleeve, through the valve bore 89, and out the lateral valve port 83. Thus, the valve bore 89 can be flushed out by introducing liquid through the hollow tube 82 while maintaining the packed bed undisturbed in the column. When the sleeve 85 is moved to the open or retracted position as shown in FIG. 4b, the end surface 86 of the sleeve is retracted within the valve bore 89 and the lateral apertures 87, 88 of the sleeve are retracted over the outer wall of the hollow tube 82, thereby blocking passage through the lateral apertures 87, 88. Drainage or filling of the column is then achieved through the lateral valve port 83.

Retractable valves of the same construction as those of FIGS. 2a, 2b, 3a, 3b, 4a, and 4b can also be incorporated into the column tube near the top of the tube, as alternatives to the spray tube 25 and associated nozzles described above and shown in FIG. 1, for cleaning the plunger 18.

Any of the injection/drainage valves depicted in FIGS. 2a, 2b, 3a, 3b, 4a, and 4b can be used as any one or all of the four valves 33 shown in FIG. 1 around the column perimeter near the base of the column. Whether the total number of injection/drainage valves at the base of the column is four as shown in FIG. 1 or some other number greater than one, one of the two valve body ports of all of the injection/drainage valves can be connected to a common conduit 91 while the other valve body port of all of the valves is connected to another common conduit 92. Also shown in FIG. 1 are a set of caster wheels 93, allowing the column support and any column mounted on it to be rolled into position within a frame that can be used to assist in the assembly, disassembly, and manipulation of the components of the column support and of the column itself. The frame can be of a construction similar to that depicted in U.S. Provisional Patent Application No. 60/869,819, filed Dec. 13, 2006, and U.S. Utility patent application Ser. No. 11/955,417, filed Dec. 13, 2007, the contents of both of which are incorporated herein by reference.

The valves described above allow the operator to pack the column with separation medium, unpack the column, i.e., remove separation medium from the column, and clean the column, all in place without removing the column from the column support. The valves can therefore be referred to as "injection/drainage valves." These valves do not reduce the surface area of the filter at the base of the column, nor do they protrude into the column to consume valuable interior volume of the column or to interfere with the flow of fluids through the column. The number of injection/drainage valves can be selected to most efficiently serve columns of different diameters, i.e., larger columns will use more valves than smaller columns. The invention also avoids the need for a column with a retractable bottom.

The following procedure can be used to transfer a slurry of separation medium from an external vessel to a column mounted in the support shown in the Figures, using injection/drainage valves of any of the types described above.

The plunger 18 (FIG. 1) is first raised while atmospheric pressure is maintained in the column. Atmospheric pressure can be maintained by deflating the inflatable seal 21 and allowing atmospheric air to enter the column as the plunger 18 is being raised, or introducing buffer solution to the column interior at the base of the column while the inflatable seal 21 remains inflated. An advantage of using a buffer solution rather than letting atmospheric air in is that the inner volume of the column can be degassed by the buffer solution and remain so until a fresh quantity of separation medium is introduced. Once the plunger is fully raised, the injection/drainage valves are opened, and slurry is injected into the column through one of the valve body ports in each of the injection/drainage valves. If the column was filled with buffer solution prior to injection, the top of the column must be kept open and buffer allowed to drain as the slurry pushes the buffer up through the top filter. A top process line will be included to facilitate the draining. After all slurry has been introduced, a quantity of buffer solution can be introduced through the same valve body ports in the injection/drainage valves to rinse the lines from the slurry supply tank up to the valve body. Once this is done, the column can be packed by lowering the plunger 18 to axially compress the slurry. Alternatively, any other conventional or obvious means of packing the slurry into a densely packed bed can be used.

Once the column is packed, it can be used for purification operations, possibly multiple such operations. The slurry must then be re-suspended and completely removed from the column. This can be achieved by connecting the top process connection to drain and introducing buffer through the inlet ports at the bottom of the column. As the buffer is being introduced, the plunger will be raised to accommodate the added buffer. The upward travel of the plunger is then terminated, and the buffer flow is reversed to enter at the top of the column and leave at the bottom. The direction of buffer flow will be reversed as necessary to help re-slurry, i.e., suspend, the solids in the previously packed bed throughout the buffer to allow the media to be removed. An alternative to re-slurring the media is to introduce air into the column through the bottom process connection at low pressure (about 5 to 10 psig).

Once the bed is re-slurried, it can be pumped out of the column. Prior to emptying the column, the injection valves and their connecting conduits can be cleaned of contaminating materials by circulating cleaning agents through the valve bores. Once the bores are cleaned, the ports are connected to a pump inlet as the valve rods are retracted. During and after the pumping process, additional buffer can be introduced into the column at either end to clean the tubes and to re-slurry any solid material that remains. The introduction of buffer at the top will serve to clean the top filter and to remove any fines that have become trapped in the filter pores. Buffer can also be introduced by a bottom process connection to re-suspend or fluidize the bed. This can help when draining the slurry through the ports 40 (FIG. 2b) and 65 (FIG. 3b), despite the short step between the bottom of the aperture and the filter 32.

While the foregoing description describes various alternatives to the components shown in the Figures, still further alternatives will be apparent to those who are skilled in the art and are within the scope of the invention. For example, in the Figures, the column tube 17, lower ring 13, and upper ring 14 are all separate components held together by the supporting rods 16. The column in this case can be glass or acrylic and the rings stainless steel. These components can be replaced by a unitary component, possibly made of steel, combining the column and the lower and upper rings and eliminating the supporting rods.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. Apparatus for preparative chromatography comprising:
   (a) a column laterally enclosed by a lateral wall and terminating at its base in a filter plate with an upper surface,
   (b) an aperture in said lateral wall substantially level with said upper surface, and
   (c) a valve comprising
      (i) a bore that opens into said aperture and has a bore axis,
      (ii) a valve body that comprises a shell and a hollow tube within said shell and coaxial with said bore,
      (iii) a sleeve slidably retained with said bore and surrounding said tube with a closure at one end, wherein said bore is shaped to restrict movement of said sleeve to a range of motion parallel to said bore axis, said range of motion extending from a closed position in which said closure is substantially flush with the inner surface of said column wall thereby closing said aperture, to an open position in which said closure is recessed within said bore thereby leaving said aperture open, and
      (iv) first and second ports in said valve body, said first port being in said shell and transverse to said bore axis, and said second port being an open end of said tube, said ports positioned such that both ports are open to said bore when said sleeve is in said closed position, thereby allowing flow communication between said first and second ports through said bore, and such that said first port is also open to said bore when said sleeve is in said open position, thereby allowing flow communication between said first port and said column through said bore and said aperture.

2. The apparatus of claim 1 wherein said second port is positioned such that said second port is closed by said plug when said plug is in said open position.

3. The apparatus of claim 1 wherein said bore is biased toward said closed position and moved to said open position upon pneumatic actuation.

4. The apparatus of claim 1 comprising a plurality of said apertures distributed along said lateral wall and distributed around said column, each said aperture substantially level with said upper surface of said filter plate.

* * * * *

UNITED STATES PATENT AND TRADEMARK OFFICE
CERTIFICATE OF CORRECTION

PATENT NO. : 7,718,058 B2
APPLICATION NO. : 12/107916
DATED : May 18, 2010
INVENTOR(S) : Maurice Agée et al.

It is certified that error appears in the above-identified patent and that said Letters Patent is hereby corrected as shown below:

In the Claims:

In column 8, claim 2, line 17, please delete "plug" and insert --sleeve--.

In column 8, claim 2, line 18, please delete "plug" and insert --sleeve--.

Signed and Sealed this
Ninth Day of July, 2013

Teresa Stanek Rea
*Acting Director of the United States Patent and Trademark Office*